United States Patent [19]

Bloxham et al.

[11] Patent Number: 5,596,074
[45] Date of Patent: Jan. 21, 1997

[54] METHOD FOR CONTROLLING COLOR FORMATION DURING POLYTETRAMETHYLENE ETHER GLYCOL PRODUCTION

[75] Inventors: Peter A. Bloxham, Houston, Tex.; Anne I. Breikss, Hockessin, Del.; Richard E. Ernst, Kennett Square, Pa.; Leon S. Scott; John D. Super, both of Wilmington, Del.; James D. Verbsky, Seabrook, Tex.

[73] Assignee: E. I. Du Pont de Nemours and Company, Wilmington, Del.

[21] Appl. No.: 577,943

[22] Filed: Dec. 22, 1995

Related U.S. Application Data

[63] Continuation of Ser. No. 495,958, Jun. 28, 1995, abandoned, which is a continuation of Ser. No. 336,356, Nov. 8, 1994, abandoned.

[51] Int. Cl.$^6$ .......................... C08G 59/00; C08G 65/34
[52] U.S. Cl. ............................... 528/417; 528/425
[58] Field of Search ........................ 528/417, 425

[56] References Cited

U.S. PATENT DOCUMENTS

| | | | |
|---|---|---|---|
| 2,870,097 | 1/1959 | Pattison | 260/2 |
| 3,726,405 | 4/1973 | Engelbrecht et al. | 210/198.2 |
| 3,852,164 | 12/1974 | Chew et al. | 203/91 |
| 4,093,633 | 6/1978 | Tanabe et al. | 549/509 |
| 4,257,961 | 3/1981 | Coates | 260/346.11 |
| 4,383,895 | 5/1983 | Ernst et al. | 203/77 |
| 4,419,189 | 12/1983 | Caracciolo | 203/77 |
| 4,480,124 | 10/1984 | Mueller | 560/248 |
| 4,590,285 | 5/1986 | Ernst | 549/509 |
| 4,590,312 | 5/1986 | Ernst | 568/861 |
| 4,940,758 | 7/1990 | Wong | 528/425 |
| 5,008,408 | 4/1991 | Fischer et al. | 549/429 |
| 5,112,943 | 5/1992 | Mueller | 528/483 |
| 5,209,825 | 5/1993 | Badat et al. | 203/29 |
| 5,288,841 | 2/1994 | Bellis et al. | 528/425 |
| 5,340,916 | 8/1994 | Henn et al. | 528/425 |

OTHER PUBLICATIONS

Hill and Carothers, Cyclic And Polymeric Formals, J Am Chem Soc, 57, 925–928, 1935.

*Primary Examiner*—Morton Foelak

[57] ABSTRACT

A process for removing precursors, such as low boiling alkyl glycols (e.g., ethylene glycol and/or 1,2-propylene glycol), to undersirable color forming acetal impurities (e.g., 1,3-dioxolane and 4-methyl-1,3-dioxolane) from technical grade 1,4-butanediol/2-methyl-1,4-butanediol mixtures and the like by distillative topping of the diol mixture prior to ring closing cyclization to corresponding tetrahydrofuran/3-methyl tetrahydrofuran mixture and subsequent polymerization to polytetramethylene glycol ether polymers. Such a process is useful to produce THF and PTMEG having a APHA color index of nearly zero.

4 Claims, No Drawings

METHOD FOR CONTROLLING COLOR FORMATION DURING POLYTETRAMETHYLENE ETHER GLYCOL PRODUCTION

This is a continuation of application Ser. No. 08/495,958 filed Jun. 28, 1995, now abandoned, which is a continuation of application Ser. No. 08/336,356 filed Nov. 8, 1994, now abandoned.

BACKGROUND OF THE INVENTION

1. Field of the Invention

This invention relates to a method of removing precursors to undesirable color forming impurities prior to production of polytertramethylene ether glycol (PTMEG) and related copolymers, more specifically, but not by way of limitation, this invention relates to an improved method of removing precursors to color forming acetals in 1,4-butanediol or mixture of 1,4-butanediol with lower alkyl-substituted 1,4-butanediols by distillation prior to the ring closing cyclization to corresponding tetrahydrofuran (THF) and 3-alkyl tetrahydrofuran (3-alkyl THF) and subsequent polymerization to produce PTMEG.

2. Description of the Related Art

It is generally known and an accepted commercial practice to manufacture PTMEG from 1,4-butanediol by first catalytically cyclizing to THF, isolating the THF and then catalytically polymerizing. It is also generally acknowledged that even purified 1,4-butanediol distillate will contain small amounts of other glycols, such as 2-methyl-1,4-butanediol as well as undersirable and difficult to separate impurities, which may lead to color control problems in the final polymer and its subsequent use. For example, in U.S. Pat. No. 5,112,943 a method of preparing a high purity polymer or copolymer by cationic polymerization of THF and, if desired, an alkylene oxide, is described in which the polymer is treated with hydrogen in the present of a hydrogenation catalyst in order to reduce the color index. This same patent indicates that technical grade THF contains small amounts of impurities in a concentration of from 10 to 500 ppm, the chemical nature of which is not known in any great detail and which cause discoloration and modify reactivity in the preparation of polyesters or polyurethanes.

Even before the above suggested hydrogenation of PTMEG polymer, it was also known that certain color forming impurities in the THF could be advantageously hydrogenated prior to polymerization. For example, in U.S. Pat. No. 4,257,961 the presence of methacrolein, dihydrofurans (2,3- and 2,5-), propionaldehyde and butyraldehydes (normal and isomeric) impurities whose presence case color formation in polymeric glycols made from THF are significantly reduced by catalytic hydrogenating dry THF.

Notwithstanding the above methods of improving color in PTMEG polymer and consistent with the admission as to lack of understanding of the chemical nature of the impurities found at the ppm level, there has been a long felt need for both better understanding and control of color formation associated with the polymerization of THF to PTMEG particularly in regards to achieving production of commercial scale quantities of polymer that exhibit virtually a zero APHA color index.

SUMMARY OF THE INVENTION

In view of the above problems and long felt need, we have now discovered a method of removing deleterious color forming precursor acetals and related impurities from commercial grade 1,4-butanediol distillate prior to ring closing cyclization and polymerization. The improved method of producing polytetramethylene ether glycol polymer or copolymer of improved color according to the instant invention involves the steps of:

(a) subjecting 1,4-butanediol liquid distillate optionally containing one or more 2-alkyl-1,4-butanediol, wherein said distillate is characterized by the presence of lower alkyl glycol impurities at a concentration range of up to about 1,000 ppm, to continuous distillation while simultaneously removing overhead a stream containing undersirable lower alkyl glycol impurities and recovering there below a stream of 1,4-butanediol optionally containing one or more 2-alkyl-1,4-butanediol substantially free of said impurities;

(b) subjecting the topped 1,4-butanediol stream produced in step (a) to catalytic cyclization thus producing tetrahydrofuran optionally containing one or more 3-alkyl-substituted tetrahydrofuran, wherein said cyclic product stream is characterized as substantially free of 1,3-dioxolane and 4-alkyl-1,3-dioxolane impurities; and (c) polymerizing the tetrahydrofuran optionally containing one or more 3-alkyl-substituted tetrahydrofuran produced in step (b) thus producing polytetramethylene ether glycol polymer of improved color index.

According to one preferred embodiment of the present invention, the starting 1,4-butanediol is itself a commercial distillate of relatively high total diol content (typically 99.9 wt % diol) which may have from trace amounts up to as much as about 16 wt % of 2-methyl-1,4-butanediol derived from the presence of formaldehyde (either produced inherently in situ or intentionally added) during the hydrogenation of butanediol used to manufactured the 1,4-butanediol (see U.S. Pat. Nos. 4,590,312 and 4,590,285).

It is an object of the present invention to provide an inexpensive and convenient commercial scale method of removing precursors to deleterious color forming impurities found in THF and polymers derived from THF. It is a further object of the present invention to provide from the removal of certain lower alkyl glycols from butanediol by distillative topping and there after the production of cyclic ethers that are essentially free of corresponding 1,3-dioxolane acetals. Fulfillment of these objects and the presence of fulfillment of additional objects will be apparent upon complete reading of the specification including the attached claims.

DESCRIPTION OF THE PREFERRED EMBODIMENTS

In view of the problems associated with color control during commercial scale production of PTMEG, we have discovered that certain low boiling impurities are present in commercial grade 1,4-butanediol (even though the 1,4-butanediol is itself a distillate) and which impurities can be removed by topping the 1,4-butanediol (i.e., by fractional distillation and removal overhead of the low boilers). More specifically, we have discovered that the removal of certain lower alkyl glycols such as ethylene glycol and propylene glycols (most particularly 1,2-propylene glycol) and other associated low boiling components from the 1,4-butanediol, with or without the presence of other 2-alkyl-1,4-butanediols, will result in the substantial absence of certain acetals in the cyclic ethers (THF and 3-alkyl THFs) produced by catalytic dehydrogenation/cyclization of the 1,4-butanediol. Furthermore, in the substantial absence of these acetals (more specifically in the absence of 1,3-dioxolane) and 4-alkyl-1,3-dioxolanes; most particularly 4-methyl-1,3-dioxolane we have found that the polymeric PTMEG produced by acidic catalysis will consistently exhibit improved color index, including when used in conjunction with other known color improving techniques an APHA color index of essentially zero.

Conformation of the presence of ethylene glycol and 1,2-propylene glycol impurities in 1,4-butanediol prior to distillative topping to remove low boilers in combination with the absence of 1,3-dioxolane and 4-methyl-1,3-dioxolane after ring closing cyclic ether formation and the resulting consistent production of PTMEG polymer of improved color index now leads us to believe that the lower alkyl glycols present in the 1,4-butanediol are, in fact, precursors to the deleterious chromophore forming acetals. Although not wanting to restrict the present invention to any single theory or explanation particularly in view of the impurities being present in very low concentration of the order of magnitude of parts per million by weight, it is, nevertheless, currently felt that under the acidic conditions of the cyclization reaction a formaldehyde source is also present and conversion of the ethylene glycol and 1,2-propylene glycol to the acetal involves a cyclic coupling with formaldehyde reminiscent of the chemistry found with respect to 7-member ring acetals and 1,3-dioxepane formation (see J. W. Hill and W. H. Carothers, J. Amer. Chem. Soc. vol. 57, pp 925+, 1935 and U.S. Pat. No. 2,870,097). Again without unduly limiting the instant invention it is felt that the 1,4-butanediol under these conditions may, itself, be the formaldehyde source, an explanation that is at least consistent with long felt need for improvement and the admission in the previously mentioned prior art U.S. Pat. No. 5,112,943 that technical grade THF contains small amounts of impurities in a concentration of from 10 to 500 ppm, the chemical nature of which is not known in any great detail and which cause discoloration and modify reactivity in the preparation of polyesters or polyurethanes.

As will be exemplified later, the intentional spiking of the 1,4-butanediol with additional ethylene glycol and 1,2-propylene glycol with and without additional spiking of formaldehyde and the resulting detection of significant increases in 1,3-dioxolane and 4-methyl-1,3-dioxolane in the topped overhead tends to support and confirm these observations and their interpreted significance (i.e., the proposed mechanistic explanation). The fact that the additional spiking was at relatively high concentrations further verifies that method according to the instant invention is operative at least over the concentration range of interest associated with the production of commercial grade THF (i.e., essentially 99.9 wt % THF).

The distillation or topping of the 1,4-butanediol liquid phase (with or without the presence of one or more 2-alkyl-1,4-butanediols) and the removal of the lower boiling glycols can be performed by any of the distillation methods and equipment as generally known and practiced in the art. Preferably and as illustrated in the Examples herein, the topping of the 1,4-butanediol is performed as a steady state distillation with the overhead containing the undesirable lower alkyl glycols (i.e., ethylene and propylene glycols) and other low boiling components. The purified 1,4-butanediol stream is removed lower on the distillation column as either a liquid or vapor as generally known in the art. It should be readily appreciated that various other configurations and equipment can be employed to accomplish the topping step and as such should be considered equivalent for purposes of this invention to that specifically illustrated herein by way of example.

The conversion of the 1,4-butanediol and 2-alkyl-1,4-butanediol to tetrahydrofuran and 3-alkyl-tetrahydrofuran, respectively, can be accomplished by any of the catalytic dehydration/cyclization reactions as generally known in the art. Typically the cyclization reaction involves the use of an acidic catalyst such as a sulfonic acid, Lewis acid, non-oxidizing mineral acid, acidic cation exchange resins or the like. For example, the cyclization reaction can be accomplished by using sulfuric acid as described in U.S. Pat. No. 3,726,405.

Preferably the THF and 3-alkyl THF produced by catalytic cyclization is dried and further refined by adjusting the pH and subjecting the cyclic ethers to a multi-stage distillation such as described in U.S. Pat. No. 4,093,633 or the like.

The polymerization of the tetrahydrofuran, with or without one or more 3-alkyl-substituted THFs, is accomplished by cationic polymerization. Generally any of the commercially acceptable acidic catalytic methods, with or without various molecular weight control agents, can be utilized: including by way of example but not by way of limitation; fluorosulfonic acid; ion exchange resin bearing the -SO$_3$H groups; carboxylic anhydrides with strong acid such as the acylium ion precursor acetic anhydride and a polymeric catalyst containing the -SO$_3$H groups and the like. Preferably fluorosulfonic acid or a polymeric resin containing -SO$_3$H groups such as Nafion® are used as the catalyst.

It is contemplated that the improved method for reducing discoloration of PTMEG according to the instant invention can also be advantageously used in combination with various other techniques for alleviating discoloration as generally known in the art. For example, while the instant process is viewed as controlling color by removal of low boiling precursors to acetal formation, previous known techniques associated with catalytic hydrogenation of other color forming impurities should also be employed when it is suspected that these other impurities are present. In particular, U.S. Pat. No. 4,257,961 describes a method of reducing the concentration of methacrolein, dihydrofuran, propionaldehyde and butyraldehyde impurities present in THF made from acetylene and formaldehyde. Preferably the hydrogenation of the THF distillate is employed in combination with the instant process as will be further illustrated in the Examples herein.

The following examples are presented to more fully demonstrate and further illustrate various individual aspects and features of the present invention while the comparative examples and showings are intended to further illustrate the differences and advantages of the present invention. As such the examples are felt to be non-limiting and are meant to illustrate the invention but are not meant to be unduly limiting in any way particularly with respect to ultimate properties of the and utility of the claimed improved process. In presenting these examples the starting material used in the non-commercial scale runs as, in fact, a commercial grade of crude 1,4-butanediols that was originally manufactured by the Reppe process (i.e., by the reaction of acetylene and formaldehyde) which had been purified and desalted by a process as essentially described in U.S. Pat. No. 3,852,164 and then stored for several months. The characterization of the concentration levels of impurities as presented in the examples is based on quantitative measurements on the actual streams at the time of use without adjusting to final PTMEG polymer composition (unless otherwise specifically stated as such).

EXAMPLE 1

In order to remove lower boiling impurities from a desalted, commercial grade mixture of 1,4-butanediol and 2-methyl-1,4-butanediol, the mixture was subject to distillation in a 20 plate 4 inch diameter Oldershaw column. The lower alkyl glycol impurities were removed from the top of the column at two different steady state boil-up to feed ratios. During distillation the 1,4-butanediol and 2-methyl-1,4-butanediol mixture was continuously fed, at room temperature, to the 15 th. plate (counting up) and the distillate totally condensed at a pressure of 50 mm Hg, part of which was taken as distillate and the remainder returned to the top plate as reflux. A portion of the bottoms was continuously removed from the twelve liter reboiler to keep it half full and represented the desired topped 1,4-butanediol and 2-methyl-1,4-butanediol product. Two steady state conditions were obtained and are identified in Table I as BDOT1 and BDOT2. The corresponding column conditions for the respective steady states are set out in the table.

TABLE I

| RATIO (wt) | BDOT1 | BDOT2 |
| --- | --- | --- |
| D/F | 0.1165 | 0.095 |
| L/D | 1.7 | 0.16 |
| V/F | 0.32 | 0.11 | where:
D = Distillate rate (grams/minute)
F = Feed rate (grams/minute)
L = Reflux rate to top plate (grams/minute)
V = Total of L + D (grams/minute)

The topped 1,4-butanediol/2-methyl-1,4-butanediol samples were then converted to tetrahydrofuran/3-methyltetrahydrofuran in a continuous cyclization unit held at 125° C. with about 4.0 wt % sulfuric acid catalyst and 7.0 grams Hastelloy-C turnings. The unit consisted of a one liter round-bottom flask with a 5 plate Oldershaw column on top, a water-cooled condenser, and a water-cooled graduated distilling receiver which could be drained into product collection containers or small bottles via a 3-way valve. Topped 1,4-butanediol/2-methyl-1,4-butanediol was pumped out of the feed container into the reaction pot. A portion of the cylized product was pumped back to the top of the Oldershaw column as reflux. Reflux ratio was controlled at about 0.3 by adjusting the reflux pump rate. The entire system was kept under a nitrogen atmosphere. Topped 1,4-butanediol/2-methyl-1,4-butanediol from run BDOT1 was fed to the cyclization unit for 34 hours, followed by topped 1,4-butanediol/2-methyl-1,4-butanediol from run BDOT2 for 29 hours.

Product from about 35–62 hours of cyclization (about 19 liters) was taken and a small amount of 50% NaOH was added to bring the pH of the material to about 11. This material was then continuously fed to a one inch diameter Oldershaw column where the azeotrope of tetrahydrofuran/3-methyltetrahydrofuran/water was removed overhead and water along with high boilers were taken out the bottom. The azeotropic distillate was then placed in a separatory funnel along with 5 grams NaOH/100 grams of azeotrope where the NaOH absorbed the water in the product and was removed as a solution of NaOH/water (approximately 50% water).

This partially dried material was then passed through a 2 inch diameter glass column packed with 4 Å molecular sieves to reduce its water content to about 0.03 wt %.

The dried product was then hydrogenated in a one-half inch diameter trickle bed reactor using Raney nickel 2800 as the catalyst. The reactor was operated at 90° C. and 130–140 psi hydrogen pressure. The hold-up time was 7–10 minutes based on liquid flow rate.

The hydrogenated product was then continuously fed to a one inch diameter Oldershaw column where most of the THF was removed overhead at a reflux ration of 3/1 and a final product consisting of approximately 50% 3-methyltetrahydrofuran in tetrahydrofuran was refined overhead away from the remaining "high boilers".

A portion of the refined tetrahydrofuran/3-methyltetrahydrofuran product (characterized as having 10 ppm of 1,3-dioxolane and no measurable 4-methyl-1,3-dioxolane) was diluted to about 30 wt % 3-methyltetrahydrofuran with tetrahydrofuran, and this solution was polymerized with flurosulfonic acid, $FSO_3H$, catalyst for four hours at 35° C. (about 200 grams THF/3-methyl THF to 22.9 grams $FSO_3H$). After quenching the catalyst with water, unreacted material was distilled off, the copolymer washed several times with water, and then lime was added for neutralization. The remaining water was then distilled off and the copolymer dried under reduced pressure at 120°–130° C. before it was filtered. The APHA color measurement of the filtered copolymer was zero.

COMPARATIVE EXAMPLE 1

In a manner analogous to previous Example 1 a desalted, commercial grade mixture of 1,4-butanediol and 2-methyl-1,4-butanediol was converted to wet THF/3-methyl THF except the starting mixture was not subjected to distillation prior to catalytic cyclization (i.e., was not topped for removal of lower boiling glycol impurities). The continuous cyclization unit was held at ~125° C. with about 4.0 wt % sulfuric acid catalyst and 7.0 g Hastelloy-C turnings. The unit consisted of a one liter round-bottom flask with a 5 plate Oldershaw column on top, a water-cooled condenser, and a water-cooled graduated distilling receiver which could be drained into product collection containers or small sample bottles via a 3-way valve. The desalted, commercial grade mixture of 1,4-butanediol and 2-methyl-1,4-butanediol was pumped out of the feed container into the reaction pot. A portion of the cyclized product was pumped back to the top of the Oldershaw column as reflux. Reflux ratio was controlled at about 0.3 by adjusting the reflux pump rate. The entire system was kept under a nitrogen atmosphere. The mixture of 1,4-butanediol and 2-methyl-1,4-butanediol was fed to the cyclization unit for 103 hours.

Product made during the last 27 hours of cyclization contained representative levels of impurities as compared to typical commercial plant cyclized product (i.e., in range of 150 to 200 ppm of each 1,3-dioxolane and 4-methyl-1,3-dioxolane). This laboratory material (about 19 liters) was taken and a small amount of 50% NaOH was added to bring the pH of the material to about 11. The material was then continuously fed to a 1 inch diameter Oldershaw column where the azeotrope of THF/3-methyl THF/water was removed overhead and water along with high boilers were taken out the bottom. The azeotropic distillate was then placed in a separatory funnel along with 5 grams NaOH/100 grams of azeotrope where the NaOH absorbed the water in the product and was removed as a solution of NaOH/Water (~50% water).

This partially dried material was then passed through a 2 inch diameter glass column packed with 4 Å molecular sieves to reduce its water content to about 0.3 wt %.

The dried product was then hydrogenated in a one-half inch diameter trickle bed reactor using Raney Ni 2800 as the catalyst. The reactor was operated at 90° C. and 130–140 psi hydrogen pressure. The hold-up time was 7–10 minutes based on liquid flow rate.

The hydrogenated product was then continuously fed to a 1 inch diameter Oldershaw column where most of the THF was removed overhead at a reflux ratio of 3/1 and a final product consisting of approximately 50 wt % 3-methyl THF in THF was refined overhead away from the remaining "high boilers".

A portion of the refined THF/3-methyl THF product was diluted to about 30 wt % 3-methyl THF with THF, and this solution was polymerized with fluorosulfonic acid catalyst for 4 hours at 35° C. (200 g THF/3-methyl THF to 23.1 g $FSO_3H$). After quenching the catalyst with water, unreacted material was distilled off, the copolymer washed several times with water, then lime was added for neutralization. The remaining water was then distilled off and the copolymer dried under reduced pressure at 120°–130° C. before it was filtered. The APHA color measurement of the filtered copolymer was 93.

EXAMPLE 2

In order to further demonstrate the effectiveness of removing impurities from 1,4-butanediol and 2-methyl-1,4-butanediol in reducing copolymer color, a desalted, commercial grade mixture of 1,4-butanediol and 2-methyl-1,4-butanediol was dewatered and then topped in two separate steps. Dewatering was done with 4 inch Oldershaw as follows:

10 Plates with feed into the Reboiler
Total Condenser
Head Pressure 300 mm Hg
Feed Preheated to ~140° C. @ 300 mm Hg
Head temp 76° C.
Pot Temp 168° C.
Reflux ratio 0.447
Feed Composition (wt %)
8.0% $H_2O$
Various Low Boiling impurities 0.4%
7.63% 2-Methyl-1,4-Butanediol
Remainder 1,4-Butanediol
Distallate (wt %)
1% THF
0.85% Very Low boilers
>0.01% 1,4-Butanediol & 2-Methyl-1,4-Butanediol
Remainder Water
Bottoms: (wt %)
0.30% Low boilers
8.22% 2-Methyl-1,4-Butanediol
1.0% Water
Remainder 1,4-Butanediol The bottoms from the above dewatering operation was topped with the following configuration:
20 Plate 4 inch Oldershaw column with feed on 10th Plate
Total Condenser
Head Pressure 50 mm Hg
Feed Preheated to 110° C. @ 50 mm Hg (Partially Flashing)
Pot Temperature 168° C.
Feed Composition: (wt %)
0.3 Low boilers
8.22% 2-Methyl-1,4-Butanediol
1.0% water
remainder 1,4-Butanediol
Bottoms Composition: (wt %)
<0.001 Low boilers
8.33% 2-Methyl-1,4-Butanediol
Remainder 1,4-Butanediol
Distillate Composition: (mole)
9.22% Low boilers
0.13% 2-Methyl-1,4-Butanediol
1.0% 1,4-Butanediol
Remainder Water
Other Results:
BDO Yield Loss 0.01%
Reflux Ratio (L/D) 18.0
Boilup/Feed (mol/mol) 0.86
Head Temperature 85° C.

Dewatered, topped 1,4-butanediol/2-methyl-1,4-butanediol was converted to tetrahydrofuran/3-methyltetrahydrofuran in a continuous cyclization unit held at ~125° C. with about 4.0 wt % sulfuric acid catalyst and 7.0 g Hastelloy-C turnings. The unit consisted of a one liter round-bottom flask with a 5 plate Oldershaw column on top, a water-cooled condenser, and a water-cooled graduated distilling receiver which could be drained into product collection containers or small sample bottles via a 3-way valve. Dewatered, topped 1,4-butanediol/2-methyl-1,4-butanediol was pumped out of the feed container into the reaction pot. A portion of the cyclized product was pumped back to the top of the Oldershaw column as reflux. Reflux ratio was controlled at about 0.3 by adjusting the reflux pump rate. The entire system was kept under a nitrogen atmosphere. Dewatered, topped 1,4-butanediol/2-methyl-1,4-butanediol was fed to the cyclization unit for about 50 hours.

Product made during 22–47 hours of cyclization (about 20 liters) was taken and a small amount of 50% NaOH was added to bring the pH of the material to about 11. The material was then continuously fed to a 1 inch diameter Oldershaw column where the azeotrope of THF/3-methyl THF/water was removed overhead and water along with high boilers were taken out the bottom. The azeotropic distillate was then placed in a separatory funnel along with 5 grams NaOH/100 grams of azeotrope where th NaOH absorbed with water in the product and was removed as a solution of NaOH/water (~50% water).

This partially dried material was then passed through a 2 inch diameter glass column packed with 4 Å molecular sieves to reduce its water content to about 0.03 wt %.

Half of the dried product was then hydrogenated in a one-half inch diameter trickle bed reactor using Raney Ni 2800 as the catalyst. The reactor was operated at 90° C. and 130–140 psi hydrogen pressure. The hold-up time was 7–10 minutes based on liquid flow rate.

The hydrogenated product was then continuously fed to a 1 inch diameter Oldershaw column where most of the THF was removed overhead at a reflux ratio of 3/1 and a final product consisting of approximately 50% 3-methyl THF in THF was refined overhead away from the remaining "high boilers".

A portion of the refined THF/3-methyl THF (characterized as having no measurable 1,3-dioxolane and <5 ppm 4-methyl-1,3-dioxolane) product was diluted to about 30 wt % 3-methyl THF with THF, and this solution was polymerized with fluorosulfonic acid catalyst for 4 hours at 35° C. (200 g THF/3-methyl THF to 22.9 g $FSO_3H$). After quenching the catalyst with water, unreacted material was distilled off, the copolymer washed several times with water, then lime was added for neutralization. The remaining water was then distilled off and the copolymer dried under reduced pressure at 120°–130° C. before it was filtered. The APHA color measurement of the filtered copolymer was 0.

EXAMPLE 3

In view of the previous examples a commercial size plant demonstration of the intentional topping of a 1,4-butanediol/ 2-methyl-1,4-butanediol stream was incorporated into a plant campaign. Prior to beginning the campaign, the butanediol topping equipment was lined out using 1,4-butanediol from normal production. The dehydration/cyclization reactor was purged more heavily than usual to reduce the amount of impurities contained in it.

During the campaign, the finishing column tops associated with recovery of the topped 1,4-butanediol/2-methyl-1,4-butanediol contained 2 to 7 wt % each ethylene and propylene glycol. No glycols or other low boilers were detected in the finishing column bottoms (i.e., desalted, topped 1,4-butanediol/2-methyl-1,4-butanediol). Initially the cyclized THF/3-methyl THF product showed 2 to 3 ppm each of 1,3-dioxolane and 4-methyl-1,3-dioxolane with 250 to 300 ppm 1,3 dioxepanes. Later in the campaign, no dioxolanes were detected in the THF/3-methyl THF product and dioxepane level had decreased to 150–200 ppm. Likewise, early in the run the high boiler bottoms contained 30–80 ppm of each dioxolane but levels dropped to <10 ppm 1,3-dioxolane and <20 ppm 4-methyl-1,3-dioxolane by the end of the campaign.

Daily samples of the high boiler bottoms (i.e., THF/3-methyl THF) were distilled and polymerized using fluorosulfonic acid catalyst. The first polymer sample was measured as 29 APHA in color. Samples from subsequent days were measures as 15, 4, and 3 APHA.

Refined THF/3-methyl THF from the campaign was collected and stored in two railcars. The first contained 51.5 wt % 3-methyl THF with 6 ppm 1,3-dioxolane and 16 ppm 4-methyl-1,3-dioxolane. The second railcar contained 47.4 wt % 3-methyl THF with 12 ppm 1,3-dioxolane and 32 ppm 4-methyl-1,3-dioxolane. In comparison, a commercial campaign about six months earlier involving the same plant and producing a similar product which was not subjected to the topping of the butanediol stream resulted in a 45.1 wt % 3-methyl THF content with 585 ppm 1,3-dioxolane and 1,246 ppm 4-methyl-1,3-dioxolane. PTMEG copolymer produced using this material as the source of 3-methyl THF typically will exhibit a 150–200 APHA color index.

EXAMPLE 4

In order to further illustrate the suspected chemical mechanism and to confirm the role of the lower alkyl glycols as precursors to dioxolane acetal formation by reaction with formaldehyde, the following experimental runs were performed. A mixture of 50 grams of 1,4-butanediol and 1 gram each of ethylene glycol, 1,2-propylene glycol, 37% formaldehyde and concentrated sulfuric acid was heated to about 140° C. until THF started to distill over. The distillation was continued until 40 grams of distillate was collected. The gas chromatographic analysis of the distillate (quantitatively reported on total organics only basis) showed 0.185% 1,3-dioxolane, 0.507% 4-methyl-1,3-dioxolane, 2.08% 1,3-dioxepane, and the balance THF (and water). the experiment was then repeated except that the formaldehyde was not added to the mixture. In this case the resulting distillate analyzed as follows: 0.001% 1,3-dioxolane, 0.004% 4-methyl-1,3-dioxolane, 0.011% 1,3-dioxepane, and the balance THF (and water).

Having thus described and exemplified the invention with a certain degree of particularity, it should be appreciated that the following claims are not to be so limited but are to be afforded a scope commensurate with the wording of each element of the claim and equivalents thereof.

We claim:

1. A method of producing polytetramethylene ether glycol polymer or copolymer of improved color comprising the steps of:

(a) subjecting 1,4-butanediol liquid distillate optionally containing one or more 2-alkyl-1,4-butanediol, wherein said distillate is characterized by the presence of lower alkyl glycol impurities at a concentration range of up to about 1,000 ppm, to continuous distillation while simultaneously removing overhead a stream containing undesirable lower alkyl glycol impurities and recovering there below a stream of 1,4-butanediol optionally containing one or more 2-alkyl-1,4-butanediol substantially free of said impurities;

(b) subjecting the topped 1,4-butanediol stream produced in step (a) to catalytic cyclization thus producing tetrahydrofuran optionally containing one or more 3-alkyl-substituted tetrahydrofuran, wherein said cyclic product stream is characterized as substantially free of 1,3-dioxolane and 4-alkyl-1,3-dioxolane impurities; and (c) polymerizing the tetrahydrofuran optionally containing one or more 3-alkyl-substituted tetrahydrofuran produced in step (b) thus producing polytetramethylene ether glycol polymer of improved color index.

2. A method of claim 1 wherein 1,4-butanediol liquid distillate contains one or more 2-alkyl-1,4-butanediol wherein the alkyl group is selected from the group consisting of methyl, ethyl, propyl, and isopropyl.

3. A method of claim 2 wherein said 2-alkyl-1,4-butanediol is 2-methyl-1,4-butanediol, said lower alkyl glycol impurities are ethylene glycol and 1,2-propylene glycol, said 3-alkyl-substituted tetrahydrofuran is and said 4-alkyl-1,3-dioxolane impurity is 4-methyl-1,3-dioxolane.

4. A method of claim 3 further comprising the steps of drying the mixture of tetrahydrofuran and 3-methyltetrahydrofuran to a water content of about 0.03 wt % and hydrogenating the dried mixture before said polymerizing step.

* * * * *